(12) United States Patent
Bonn

(10) Patent No.: US 9,024,237 B2
(45) Date of Patent: May 5, 2015

(54) MATERIAL FUSING APPARATUS, SYSTEM AND METHOD OF USE

(75) Inventor: Kenlyn S. Bonn, Boulder, CO (US)

(73) Assignee: Covidien LP, Mansfield, MA (US)

( * ) Notice: Subject to any disclaimer, the term of this patent is extended or adjusted under 35 U.S.C. 154(b) by 898 days.

(21) Appl. No.: 12/568,838

(22) Filed: Sep. 29, 2009

(65) Prior Publication Data

US 2011/0073594 A1    Mar. 31, 2011

(51) Int. Cl.
| | | |
|---|---|---|
| *H05B 6/64* | (2006.01) | |
| *A61B 18/18* | (2006.01) | |
| *H05B 6/80* | (2006.01) | |
| A61B 18/00 | (2006.01) | |

(52) U.S. Cl.
CPC ...... *A61B 18/18* (2013.01); *H05B 6/64* (2013.01); *H05B 6/80* (2013.01); *A61B 18/1815* (2013.01); *A61B 2018/0019* (2013.01); *A61B 2018/1853* (2013.01)

(58) Field of Classification Search
None
See application file for complete search history.

(56) References Cited

U.S. PATENT DOCUMENTS

| | | |
|---|---|---|
| D223,367 S | 4/1972 | Kountz |
| D249,549 S | 9/1978 | Pike |
| D263,020 S | 2/1982 | Rau, III |
| D266,842 S | 11/1982 | Villers et al. |
| D278,306 S | 4/1985 | McIntosh |
| 4,597,379 A | 7/1986 | Kihn et al. |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,218 S | 1/1995 | Van de Peer |
| D354,564 S | 1/1995 | Medema |
| D358,887 S | 5/1995 | Feinberg |
| D384,413 S | 9/1997 | Zlock et al. |

(Continued)

FOREIGN PATENT DOCUMENTS

| | | |
|---|---|---|
| CN | 1103807 | 6/1995 |
| CN | 201299462 | 9/2009 |

(Continued)

OTHER PUBLICATIONS

Anonymous. Blunt Tubes with Finished Ends. Pointed Cannula, Popper & Sons Biomedical Instrument Division, (Products Price List), one page, Jul. 19, 2000.

(Continued)

*Primary Examiner* — Johannes P Mondt

(57) ABSTRACT

A microwave material fusing apparatus for fusing two or more layers of material is disclosed. The apparatus includes an end effector including a radiating strike plate and a non-radiating fusing arm. The radiating strike plate is adapted to receive microwave energy from a microwave energy source and configured to radiate microwave energy therefrom upon selective activation of the microwave energy source. The non-radiating fusing arm is disposed in substantial opposition to the radiating strike plate and includes a conductive tip on the distal end. The conductive tip of the non-radiating fusing arm is configured to compress material therebetween such that upon activation of the microwave energy source, microwave energy is transferred between the radiating strike plate and the conductive tip to fuse the material disposed therebetween.

15 Claims, 7 Drawing Sheets

(56) References Cited

U.S. PATENT DOCUMENTS

| | | | |
|---|---|---|---|
| 5,707,369 A | 1/1998 | Vaitekunas et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| 6,024,743 A | 2/2000 | Edwards | |
| D424,693 S | 5/2000 | Pruter | |
| D424,694 S | 5/2000 | Tetzlaff et al. | |
| D425,201 S | 5/2000 | Tetzlaff et al. | |
| 6,122,549 A | 9/2000 | Sharkey et al. | |
| H1904 H | 10/2000 | Yates et al. | |
| 6,224,593 B1 | 5/2001 | Ryan et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,485,489 B2 | 11/2002 | Teirstein et al. | |
| D487,039 S | 2/2004 | Webster et al. | |
| 6,723,092 B2 | 4/2004 | Brown et al. | |
| D493,888 S | 8/2004 | Reschke | |
| 6,773,409 B2 | 8/2004 | Truckai et al. | |
| 6,786,905 B2 | 9/2004 | Swanson et al. | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| 7,226,446 B1* | 6/2007 | Mody et al. | 606/33 |
| D547,154 S | 7/2007 | Lee | |
| 7,270,664 B2* | 9/2007 | Johnson et al. | 606/51 |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D576,932 S | 9/2008 | Strehler | |
| D582,038 S | 12/2008 | Swoyer et al. | |
| D594,736 S | 6/2009 | Esjunin | |
| D594,737 S | 6/2009 | Kelly et al. | |
| D606,203 S | 12/2009 | Husheer et al. | |
| 7,625,370 B2 | 12/2009 | Hart et al. | |
| D613,412 S | 4/2010 | DeCarlo | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D634,010 S | 3/2011 | DeCarlo | |
| 7,967,839 B2 | 6/2011 | Flock et al. | |
| D649,249 S | 11/2011 | Guerra | |
| D649,643 S | 11/2011 | Allen, IV et al. | |
| 8,075,580 B2 | 12/2011 | Makower | |
| 8,147,485 B2 | 4/2012 | Wham et al. | |
| D661,394 S | 6/2012 | Romero et al. | |
| 8,251,993 B2 | 8/2012 | Luttich | |
| 2003/0069570 A1 | 4/2003 | Witzel et al. | |
| 2003/0216732 A1 | 11/2003 | Truckai et al. | |
| 2004/0073238 A1 | 4/2004 | Makower | |
| 2004/0073256 A1 | 4/2004 | Marchitto et al. | |
| 2004/0210282 A1 | 10/2004 | Flock et al. | |
| 2006/0271030 A1* | 11/2006 | Francis et al. | 606/27 |
| 2007/0043337 A1* | 2/2007 | McAuley | 606/1 |
| 2007/0173811 A1 | 7/2007 | Couture et al. | |
| 2007/0260235 A1 | 11/2007 | Podhajsky | |
| 2007/0265616 A1 | 11/2007 | Couture et al. | |
| 2008/0015575 A1 | 1/2008 | Odom et al. | |
| 2008/0021450 A1 | 1/2008 | Couture | |
| 2008/0033428 A1 | 2/2008 | Artale et al. | |
| 2008/0045947 A1* | 2/2008 | Johnson et al. | 606/51 |
| 2008/0091189 A1 | 4/2008 | Carlton | |
| 2008/0195093 A1* | 8/2008 | Couture et al. | 606/45 |
| 2009/0157075 A1 | 6/2009 | Wham et al. | |
| 2009/0248007 A1 | 10/2009 | Falkenstein et al. | |
| 2009/0248013 A1 | 10/2009 | Falkenstein et al. | |
| 2009/0248019 A1 | 10/2009 | Falkenstein et al. | |
| 2009/0248020 A1* | 10/2009 | Falkenstein et al. | 606/45 |
| 2009/0248022 A1 | 10/2009 | Falkenstein et al. | |
| 2010/0049194 A1 | 2/2010 | Hart et al. | |

FOREIGN PATENT DOCUMENTS

| | | |
|---|---|---|
| DE | 390937 | 3/1924 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2514501 | 10/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3423356 | 6/1986 |
| DE | 3510586 | 10/1986 |
| DE | 3612646 | 4/1987 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10031773 | 11/2001 |
| DE | 20121161 | 4/2002 |
| DE | 10045375 | 10/2002 |
| DE | 10224154 | 12/2003 |
| DE | 10310765 | 9/2004 |
| DE | 10328514 | 3/2005 |
| DE | 10 2004 026179 | 12/2005 |
| DE | 102004022206 | 12/2005 |
| DE | 202005015147 | 3/2006 |
| DE | 20 2007 003318 | 8/2007 |
| DE | 20 2007 009165 | 10/2007 |
| DE | 20 2007 009317 | 10/2007 |

(56) References Cited

FOREIGN PATENT DOCUMENTS

| | | |
|---|---|---|
| DE | 20 2007 016233 | 3/2008 |
| DE | 19738457 | 1/2009 |
| DE | 10 2008 018406 | 7/2009 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 1159926 | 12/2001 |
| EP | 1186274 | 3/2002 |
| EP | 0 648 515 | 4/2003 |
| FR | 179 607 | 11/1906 |
| FR | 1 275 415 | 9/1960 |
| FR | 1 275 415 | 10/1961 |
| FR | 1 347 865 | 11/1963 |
| FR | 2 276 027 | 6/1974 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 573 301 | 5/1986 |
| FR | 2 862 813 | 5/2005 |
| FR | 2 864 439 | 7/2005 |
| JP | 61-501068 | 9/1984 |
| JP | 6-502328 | 3/1992 |
| JP | 65-502328 | 3/1992 |
| JP | 5-5106 | 1/1993 |
| JP | 5-40112 | 2/1993 |
| JP | 05-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 06343644 | 12/1994 |
| JP | 7-265328 | 10/1995 |
| JP | 07265328 | 10/1995 |
| JP | 8-56955 | 3/1996 |
| JP | 8-317936 | 3/1996 |
| JP | 08056955 | 3/1996 |
| JP | 8-289895 | 5/1996 |
| JP | 8-252263 | 10/1996 |
| JP | 08252263 | 10/1996 |
| JP | 8-317934 | 12/1996 |
| JP | 9-10223 | 1/1997 |
| JP | 09000492 | 1/1997 |
| JP | 09010223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 11244298 | 9/1999 |
| JP | 2000-342599 | 12/2000 |
| JP | 2000-350732 | 12/2000 |
| JP | 2000342599 | 12/2000 |
| JP | 2000350732 | 12/2000 |
| JP | 2001-8944 | 1/2001 |
| JP | 2001003776 | 1/2001 |
| JP | 2001008944 | 1/2001 |
| JP | 2001-29356 | 2/2001 |
| JP | 2001029356 | 2/2001 |
| JP | 2001037775 | 2/2001 |
| JP | 2001-128990 | 5/2001 |
| JP | 2001128990 | 5/2001 |
| JP | 2001-190564 | 7/2001 |
| JP | 2001231870 | 8/2001 |
| JP | 2002-136525 | 5/2002 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-253789 | 9/2005 |
| JP | 2006-015078 | 1/2006 |
| JP | 2006-501939 | 1/2006 |
| JP | 2006-095316 | 4/2006 |
| JP | 2008142467 | 6/2008 |
| JP | 2011-125195 | 6/2011 |
| SU | 166452 | 11/1964 |
| SU | 401367 | 11/1974 |
| SU | 727201 | 4/1980 |
| WO | WO00/36985 | 6/2000 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | WO 03/068046 | 8/2003 |
| WO | WO 2005/110264 | 11/2005 |
| WO | WO 2006/021269 | 3/2006 |
| WO | WO 2008/040483 | 4/2008 |
| WO | WO 2009/124097 | 10/2009 |
| WO | WO2010/035831 | 4/2010 |

OTHER PUBLICATIONS

C. F. Gottlieb et al., "Interstitial Microwave Hyperthermia Applicators having Submillimetre Diameters", Int. J. Hyperthermia, vol. 6, No. 3, pp. 707-714, 1990.
Cosman et al., "Methods of Making Nervous System Lesions" In William RH, Rengachary SS (eds): Neurosurgery, New York: McGraw•Hill, vol. 111, (1984), pp. 2490-2499.
Esterline, "Light Key Projection Keyboard" 2004 Advanced Input Systems, located at: <http://www.advanced-input.com/lightkey> last visited on Feb. 10, 2005.
Goldberg et al., "Image-guided Radiofrequency Tumor Ablation: Challenges and Opportunities—Part 1", (2001) J Vasc. Interv. Radiol, vol. 12, pp. 1021-1032.
Humphries Jr. et al., "Finite•Element Codes to Model Electrical Heating and Non•LInear Thermal Transport in Biological Media", Proc. ASME HTD-355, 131 (1997).
Livraghi et al., (1995) "Saline-enhanced RF Tissue Ablation in the Treatment of Liver Metastases", Radiology, pp. 205-210.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Stuart W. Young, Nuclear Magnetic Resonance Imaging—Basic Principles, Raven Press, New York, 1984.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Vallfors et al., "Automatically Controlled Bipolar Electrocoagulation-'COA-COMP'" Neurosurgical Review 7:2-3 (1984) pp. 187-190.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
McLellan et al. "Vessel Sealing for Hemostasis During Pelvic Surgery" Int'l Federation of Gynecology and Obstetrics FIGO World Congress 2000, Washington, D.C.
European Search Report EP 06006963 dated Jul. 25, 2006.
European Search Report EP 07015191.5 dated Jan. 23, 2007.
European Search Report EP 07015601.3 dated Jan. 4, 2007.
International Search Report PCT/US04/15311 dated Jan. 12, 2004.
Int'l Search Report PCT/US03/28534dated Dec. 19, 2003.
U.S. Appl. No. 08/136,098, filed Oct. 14, 1993, Roger A. Stern.

(56) References Cited

OTHER PUBLICATIONS

U.S. Appl. No. 08/483,742, filed Jun. 7, 1995, Roger A. Stern.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,753, filed Jan. 6, 2012, Lee et al.
U.S. Appl. No. 13/344,790, filed Jan. 6, 2012, Lee et al.
U.S. Appl. No. 13/400,223, filed Feb. 20, 2012, Anthony B. Ross.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,307, filed May 22, 2012, Casey M. Ladtkow.
U.S. Appl. No. 13/477,320, filed May 22, 2012, Joseph D. Brannan.
U.S. Appl. No. 13/483,858, filed May 30, 2012, Francesca Rossetto.
U.S. Appl. No. 13/488,964, filed Jun. 5, 2012, Steven P. Buysse.
U.S. Appl. No. 13/525,853, filed Jun. 18, 2012, Joseph A. Paulus.
U.S. Appl. No. 13/526,676, filed Jun. 19, 2012, Francesca Rossetto.
U.S. Appl. No. 13/539,650, filed Jul. 2, 2012, Joseph A. Paulus.
U.S. Appl. No. 13/539,690, filed Jul. 2, 2012, Steven P. Buysse.
U.S. Appl. No. 13/539,725, filed Jul. 2, 2012, Steven P. Buysse.
U.S. Appl. No. 13/539,875, filed Jul. 2, 2012, Mani N. Prakash.
U.S. Appl. No. 13/551,005, filed Jul. 17, 2012, Chris Rusin.
U.S. Appl. No. 13/567,624, filed Aug. 6, 2012, Mani N. Prakash.
U.S. Appl. No. 13/568,679, filed Aug. 7, 2012, Robert J. Behnke, II.
U.S. Appl. No. 13/596,785, filed Aug. 28, 2012, Richard A. Willyard.
U.S. Appl. No. 13/598,141, filed Aug. 29, 2012, Kenlyn S. Bonn.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division. (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave. Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.

(56) References Cited

OTHER PUBLICATIONS

Humphries Jr. et al., "Finite Element Codes to Model Electrical Heating and Non LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, VOL., BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology, 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.

(56) References Cited

OTHER PUBLICATIONS

Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.

(56) References Cited

OTHER PUBLICATIONS

European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Oct. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009392.1 extended dated Sep. 19, 2011.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161.722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11000669.9 extended dated Jun. 30, 2011.
European Search Report EP 11001596.3 extended dated Jul. 4, 2011.
European Search Report EP 11001872.8 extended dated Jul. 6, 2011.
European Search Report EP 11004942 dated Oct. 4, 2011.
European Search Report EP 11009036.2 dated Feb. 13, 2012.
European Search Report EP 11010024.5 dated Apr. 20, 2012.
European Search Report EP 11010046.8 dated Apr. 17, 2012.
European Search Report EP 11010093.0 dated Mar. 27, 2012.
European Search Report EP 11010175.5 dated May 10, 2012.
European Search Report EP 11010176.3 dated Apr. 2, 2012.
European Search Report EP 11010177.1 dated May 10, 2012.
European Search Report EP 11174318.3 dated Nov. 7, 2011.
European Search Report EP 11185926.0 dated Feb. 3, 2012.
European Search Report EP 12000334.8 dated May 4, 2012.
European Search Report EP 12000335.5 dated May 10, 2012.
European Search Report EP 12000336.3 dated May 14, 2012.
European Search Report EP 12001841.1 dated Jul. 16, 2012.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated, Aug. 27, 2004.
International Search Report PCT/US04/13273 dated Dec. 15,2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
International Search Report EP10011750 dated Feb. 1, 2011.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.

(56) References Cited

OTHER PUBLICATIONS

U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/464,569, filed May 4, 2012, Duane E. Kerr.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,543, filed May 14, 2012, Sean T. Dycus.
U.S. Appl. No. 13/470,775, filed May 14, 2012, James D. Allen, IV.
U.S. Appl. No. 13/470,797, filed May 14, 2012, John J. Kappus.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/488,093, filed Jun. 4, 2012, Kristin D. Johnson.
U.S. Appl. No. 13/491,853, filed Jun. 8, 2012, Jessica E. Olson.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/550,322, filed Jul. 16, 2012, John J. Kappus.
U.S. Appl. No. 13/571,055, filed Aug. 9, 2012, Paul Guerra.
U.S. Appl. No. 13/571,821, filed Aug. 10, 2012, Joseph D. Bucciaglia.
U.S. Appl. No. 13/584,194, filed Aug. 13, 2012, Sean T. Dycus.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectomy" American College of Surgeons (ACS) Clinicla Congress Poster (2000).
Muller et al., "Extended Left Hemicolectomy Using the LigaSure Vessel Sealing SyStem" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" • Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

Strasberg et al., "Use of a Bipolar Vessel-Sealing Device for Parenchymal Transection During Liver Surgery" Sournal of Gastrointestinal Surgery, vol. 6, No. 4, Jul./Aug. 2002 pp. 569-574.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hdmostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05004431.2 dated Jun. 2, 2005.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020528.9 dated Aug. 4, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 015215.8 dated Feb. 24, 2010.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205,3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175559.3 dated May 25, 2012.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019.9 dated Aug. 22, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 006233.8 dated Feb. 2, 2012.
Int'l Search Report EP 11 007972.0 dated Dec. 28, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.

(56) References Cited

OTHER PUBLICATIONS

Int'l Search Report EP 11 153503.5 dated Mar. 5, 2012.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 168419.7 dated Oct. 20, 2011.
Int'l Search Report EP 11 164274.0 dated Aug. 3, 2011.
Int'l Search Report EP 11 164275.7. dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report EP 11 180183 dated Nov. 30, 2011.
Int'l Search Report EP 11 183265.5 dated Nov. 28, 2011.
Int'l Search Report EP 11 183476.8 dated Jan. 18, 2012.
Int'l Search Report EP 11 185028.5 dated Jan. 2, 2012.
Int'l Search Report EP 11 189521.5 dated Feb. 20, 2012.
Int'l Search Report EP 11 190723.4 dated Mar. 16, 2012.
Int'l Search Report EP 12 155726.8 dated May 25, 2012.
Int'l Search Report EP 12 155728.4 dated Jul. 4, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

MATERIAL FUSING APPARATUS, SYSTEM AND METHOD OF USE

BACKGROUND

1. Technical Field

The present invention relates to a material fusing apparatus, system and methods therefore, wherein the procedure includes the generation and transfer of energy from an energy source to a material fusing apparatus and periodic delivery of a burst of focused energy to material.

2. Description of Related Art

Microwave energy has proven to be an effective means of performing electrosurgical ablation procedures. Research in the electrosurgical microwave ablation field has produced may different types of microwave ablation probes such as, for example, percutaneous probes that are inserted to a target tissue through the skin, surgical probes that are inserted into tissue during a surgical procedure and deployable probes that are inserted into a position in a first condition and deployed to a second condition.

Research in the electrosurgical microwave ablation field has also resulted in new and inventive ways of delivering microwave energy and monitoring the delivery of microwave energy. Various microwave research tools have allowed researchers to better observe and understand how microwaves and microwave delivery devices behave in tissue and how this behavior changes over time. Researchers have also developed new and novel ways of monitoring the energy delivered to an ablation device and have developed systems to combining phase-shifted microwave waveforms and systems and devices to delivery microwave energy at two or more frequencies.

Microwave energy delivery research, and its use in the electrosurgical ablation field, has also led to research with microwave energy delivery devices, material fusing apparatuses, systems and methods of use.

SUMMARY

The present disclosure relates to a microwave material fusing apparatus and control system for use in performing a material fusing procedure. In one embodiment, the microwave material fusing apparatus includes an end effector including a radiating strike plate and a non-radiating fusing arm. The radiating strike plate is adapted to receive microwave energy from a microwave energy source and configured to radiate microwave energy therefrom upon selective activation of the microwave energy source. The non-radiating fusing arm is disposed in substantial opposition to the radiating strike plate and including a conductive tip on a distal end. The conductive tip of the non-radiating fusing arm and the radiating strike plate are selectably movable relative to one another to compress material therebetween such that upon activation of the microwave energy source, microwave energy is transferred between the radiating strike plate and the conductive tip to fuse the material disposed therebetween.

The end effector of the microwave material fusing apparatus is configured to release a burst of focused energy that travels between the conductive tip and the radiating strike plate to fuse material.

The end effector of the microwave material fusing apparatus may further include a closure mechanism connected to the radiating strike plate and the non-radiating fusing arm. In a first condition, the closure mechanism positions the radiating strike plate and the non-radiating fusing aim in a spaced spaced-apart relationship. In a second condition, the closure mechanism positions the radiating strike plate and the conductive tip of the non-radiating fusing arm such that a material fusing gap is formed therebetween. The material fusing gap between the radiating strike plate and the conductive tip of the non-radiating fusing arm in the second condition is related to one or more of a property of the material therebetween, the density of the radiated microwave energy and the amount of energy delivered to the material.

The energy level of the microwave energy signal is related to the material fusing gap between the conductive tip and the radiating strike plate and a dielectric properties of the material between the conductive tip and the radiating strike plate. Microwave energy is transferred between the conductive tip of the non-radiating fusing arm and the strike point of the radiating strike plate. The strike point may be the radial center formed on the radiating strike plate. Material fusing may be initiated after the material fusing gap meets a threshold distance between the conductive tip and the radiating strike plate.

The closure mechanism may be pivotally attached to the radiating strike plate and to the non-radiating fusing arm, wherein the radiating strike plate and the non-radiating fusing arm rotate relative to one another to compress the material. The closure mechanism may be slidably attached to the radiating strike plate and the non-radiating fusing arm such that the radiating strike plate and the non-radiating fusing arm rotate relative to one another in a parallel manner to compress the material.

The end effector may further include a clamping trigger, connected to the closure mechanism. The clamping trigger is configured to actuate the closure mechanism between the first condition and the second condition. Material fusing may be initiated after the applied pressure exceeds a threshold. The radiating strike plate and the non-radiating fusing arm may be adapted to fuse tissue.

The present disclosure also describes a method of fusing material. The method includes the steps of: providing an end effector including a radiating strike plate adapted to receive microwave energy from a microwave energy source and configured to radiate microwave energy therefrom upon selective activation of the microwave energy source and a non-radiating fusing arm disposed in substantial opposition to the radiating strike plate, the non-radiating fusing arm including a conductive tip on a distal end thereof; compressing material between the radiating strike plate and the conductive tip of the non-radiating fusing arm; and activating the microwave energy source to transmit energy between the radiating strike plate and the conductive tip to fuse the material disposed therebetween.

The present disclosure describes a system for fusing material and includes a microwave generator configured to generate a microwave energy signal and a material fusing apparatus connected to the microwave generator by a microwave energy transmission line. The material fusing apparatus further includes an end effector including a radiating strike plate adapted to receive microwave energy from the microwave generator and being configured to radiate microwave energy therefrom upon selective activation of the microwave generator and a non-radiating fusing arm disposed in substantial opposition to the radiating strike plate, the non-radiating fusing arm including a conductive tip on a distal end thereof.

The end effector may be configured to release a burst of focused energy that travels between the conductive tip and the radiating strike plate to fuse the material therebetween.

The end effector may further include a closure mechanism connected to the radiating strike plate and the non-radiating fusing arm. In a first condition, the closure mechanism may position the radiating strike plate and the non-radiating fusing arm in a spaced-apart relationship. In a second condition, the closure mechanism may position the radiating strike plate and the conductive tip of the non-radiating fusing arm such that a material fusing gap is formed therebetween.

The material fusing gap between the radiating strike plate and the conductive tip of the non-radiating fusing arm in the second condition may be related to a property of the material therebetween, the density of the radiated microwave energy and/or the amount of energy delivered to the material. The energy level of the microwave energy signal may be related to the material fusing gap between the conductive tip and the radiating strike plate and a dielectric property of the material between the conductive tip and the radiating strike plate. Microwave energy is transferred between the conductive tip and a strike point formed on the radiating strike plate.

In another embodiment, material fusing may be initiated after the material fusing gap meets a threshold. The radiating strike plate and the non-radiating fusing arm may be adapted to fuse tissue.

DETAILED DESCRIPTION

Detailed embodiments of the present disclosure are described herein, however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
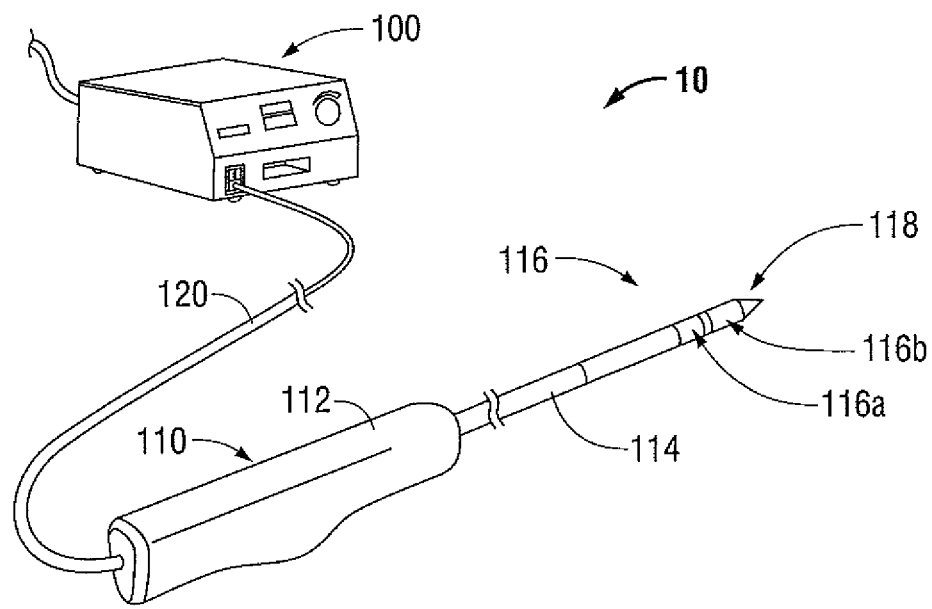
FIG. 1 is a schematically-illustrated view of a microwave energy delivery system including a microwave generator and a microwave energy delivery device in accordance with one embodiment of the present disclosure.

Referring now to FIG. 1, a microwave ablation system is shown as system 10. System 10 includes a microwave signal generator 100 connected to a typical microwave energy delivery device 110 via a transmission line 120.

Microwave energy delivery device 110 includes a handle 112 having an elongated shaft 114 that extends therefrom and including an antenna 116 on a distal end thereof. Distal portion of antenna 116 may form a sharpened radiating tip 118. Antenna 116 may be a dipole antenna with a proximal radiating section 116a and a distal radiating section 116b.

Figure 2:
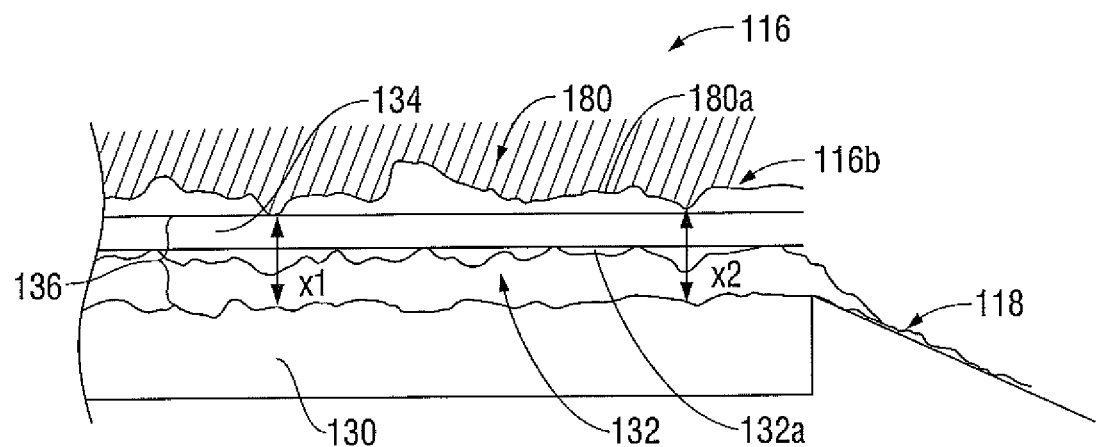
FIG. 2 is a cross-sectional view of the surface (at a microscopic level) of an antenna portion of the microwave energy delivery device of FIG. 1 illustrating a fusing phenomenon in accordance with one embodiment of the present disclosure.

FIG. 2 is a detailed cross-sectional view of the surface (at a microscopic level) of a portion of the distal radiating section 116b of the microwave energy delivery device 110 of FIG. 1. The surface of the distal radiating section 116b includes a metal substrate 130 covered by a spray coating 132 of polytetrafluoroethylene or polytetrafluoroethene (hereinafter PTFE) such as a spray PTFE sold under the trademark Teflon® and manufactured by DuPont of Wilmington, Del.

The metal substrate 130 and spray coating 132 is covered by a PTFE shrink wrap tubing layer 134. The PTFE shrink wrap tubing 134 used to cover the spray coating 132 and the metal substrate 130 is typically formed by extrusion and stretched into a thin tube and placed over the antenna 116. Applying heat to the PTFE shrink wrap tubing 134 while on the antenna 116 draws the thin tube toward the spray coating 132 thus forming a two layer PTFE surface 136 on the metal substrate 130. The two layer PTFE surface 136 forms a non-uniform thickness at various cross-sectional locations.

The PTFE spray coating 132 and the PTFE shrink wrap tubing 134 are two distinct and separate layers. The heat applied to shrink the PTFE shrink wrap tubing 134 is not capable of melting the layers of the PTFE or fusing the layers 132, 134 together since the melting point of PTFE is about 327° C.

With continued reference to FIGS. 1 and 2, in use the antenna portion 116 is placed in patient tissue 180. During a typical microwave ablation procedure the antenna 116 of the microwave energy delivery device 110 delivers microwave energy to the patient tissue 180. Ablation typically occurs by holding the temperatures of patient tissue above 40° C. for a period of time. During these procedures, the patient tissue temperatures typically do not exceed 100° C. (i.e., the boiling point of water) because production of steam during an ablation procedure is undesirable.

One effect of microwave energy delivery may be the forming of a layer of carbon, commonly know as "char" 180a, on the surface of the patient tissue 180 adjacent the antenna 116. The formation of this layer of char 180a on patient tissue 180 is the result of tissue dehydration and tissue heating.

In laboratory testing it was observed that applying microwave energy at high power levels would result in the fusing of the spray coating 132 and the PTFE shrink wrap tubing layer 134 at what appeared to be random points on the antenna 116. The areas of fusion were small but relevant since the magnetic field portion of the antenna 116 changed as a result of these formations. It was observed that the size and number of fused points was related to the size (i.e., length and diameter) of the radiating section and the coating material. For example, it was observed that a distal radiating section of an antenna covered with PTFE having an outer diameter of about 2.1 mm and a length of about 10 mm would generate 2 to 3 regions of irregularly shaped fusion points of about 0.5 to 1.5 mm each.

The two PTFE layers 132, 134 form a dielectric layer that provides a dielectric barrier between the radiating metal substrate 130 and patient tissue 180. The irregularities in surface of the metal substrate 130, the irregularities in the thickness of the PTFE spray coating 132 and varying thickness of the PTFE shrink wrap tubing layer 134 all contribute to the formation of this dielectric barrier of varying thickness, thus varying strength, across the surface of the antenna 116. Varying the dielectric strength contributes to the randomness of the fusing locations of the two PTFE layers 132, 134.

It was also observed that the layer of char 180a, located on the patient tissue 180 surface adjacent the antenna 116, also formed an irregularly patterned surface. As such, at any point on the antenna 116, the distances between the char 180a and the surface of the metal substrate 130 varied. Since char 180a is more conductive than patient tissue 180 the formation of char 180a changes the concentration of the magnetic fields between the char 180a and the metal substrate 130.

These factors, the irregularities in the surface of the char 180a, the varying distance between the char 180a to the metal substrate 130 and irregularities in the combined thickness of the two layer PTFE layers 132, 134, all contribute to changes in the magnetic field densities along the surface of the metal substrate 130. For example, at positions X1 and X2 the thickness of the dielectric barrier, (e.g., the thickness of the PTFE spray coating 132 and the thickness of the PTFE shrink wrap tubing layer 134) is less than the surrounding area. In addition, at positions X1 and X2 char 180a, and the irregular surface of the char 180a, the magnetic field lines are stronger. As a result, at higher energy levels the increased field concentrations, reduced thickness of the dielectric barrier and the position of the char 180a with respect to the metal substrate all contribute to a breakdown of the dielectric layer 132, 134 at positions X1 and X2 along the surface of the antenna 116.

At each dielectric breakdown point X1, X2 current conducts between the metal substrate 130 and the char coating 180a on the patient tissue 180. As evidence of this phenomenon the two PTFE layers 132, 134 fuse together. As such, the temperature of both PTFE layers 132, 134 exceeded the PTFE melting point of about 327° C.

The breakdown phenomenon is further characterized as a periodic delivery of a burst of focused energy that is delivered between the metal substrate 130 and patient tissue 180. The burst of focused energy resembles a "lightning strike" in which a momentary flow of energy between the metal substrate 130 and char 180a produced a large amount of heat in a small area. The heat generated in each of these locations is sufficient to fuse the two layers of PTFE (i.e., the temperature exceeded melting point of PTFE or at least 327° C.) but localized and/or of a short enough duration as to confine the heat generation to this small area.

To verify this phenomenon a microwave energy delivery device 110 was configured to deliver a high power microwave energy signal in free space (i.e., in the absence of patient tissue). The antenna 116 of the microwave energy delivery device 110, when placed in contact with a carbon granule, produced a burst of focused energy as discussed hereinabove, at the point of contact between the carbon granule and the antenna 116. The PTFE shrink wrap tubing layer 134 was cut longitudinally away from the carbon particle contact point to facilitate the removal of the PTFE shrink wrap tubing layer 134 from the antenna 116. Removal of the PTFE shrink wrap tubing 134 verified that at the point of contact between the antenna and each carbon granule resulted in the fusing of the two PTFE layers 132, 134.

Figure 3:
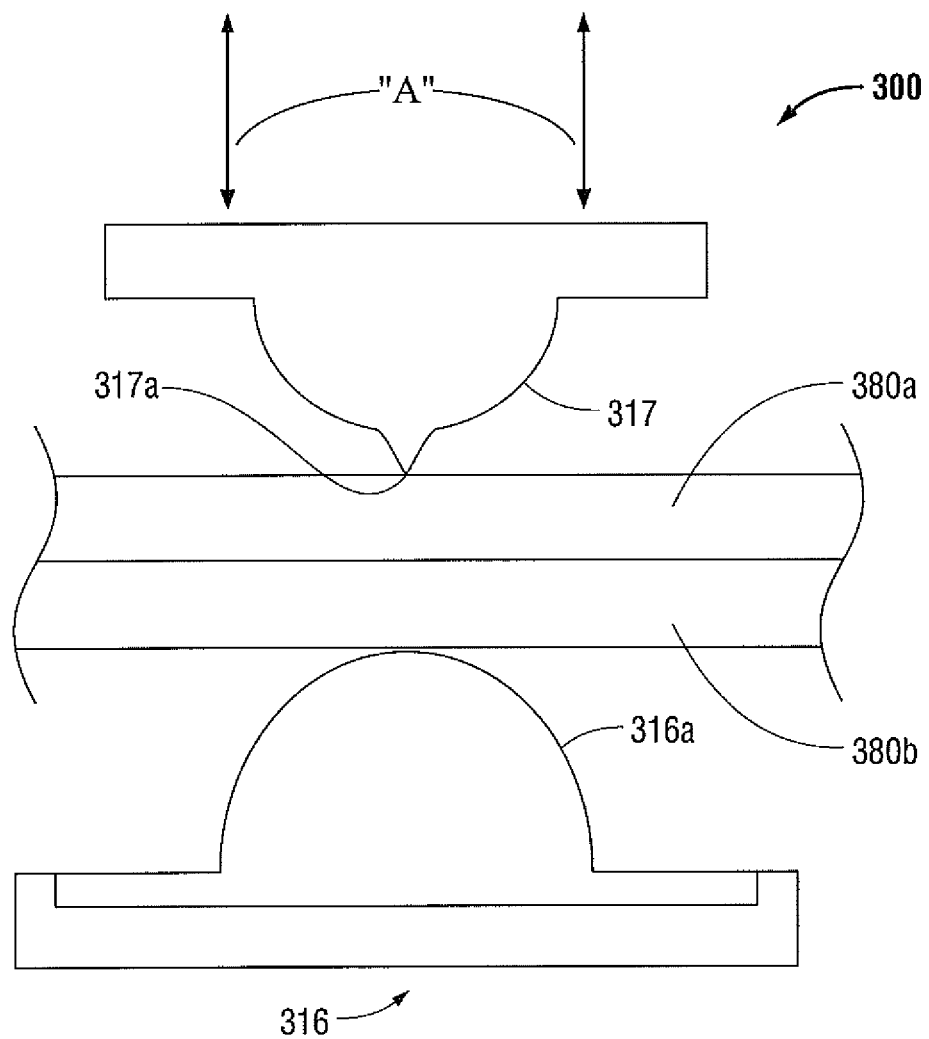
FIG. 3 is an illustration of a dielectric fusing apparatus according to one embodiment of the present disclosure.

FIG. 3 is an illustration of a dielectric fusing apparatus 300 according to one embodiment of the present disclosure. The dielectric fusing apparatus 300 includes an upper member 317 and a lower member 316. Upper member 317 includes a conductive tip 317a on the portion of the upper member 317 closest to the lower member 316. Metal radiating section 316a of the lower member 316 is formed of any suitable uncoated metal and configured to radiate microwave energy therefrom. With reference to FIGS. 2 and 3, the metal radiating section 316a and the conductive tip 317a are analogous to the metal substrate 130 and the char 180a on the patient tissue 180, respectively.

A first layer 380a of material and a second layer 380b of material are placed between the upper member 317 and the lower member 316 such that at least a portion of the first and second layers 380a, 380b of material cover the lower member 316 and are positioned between the conductive tip 317a and the metal radiating section 316a. The first and second layers 380a, 380b of material may be any suitable dielectric materials, such as, for example, two PTFE layers or two tissue layers. Layers 380a, 380b of material do not need to be similar in structure as the fusing apparatus may effectively fuse materials that do not normally bond together.

To fuse the first and second layers 380a, 380b the conductive tip 317a is moved toward the lower member 316 while the metal radiating section 316a is provided a microwave energy signal and radiates microwave energy. Movement of the conductive tip 317a toward the metal radiating section 316a strengthens the magnetic field generated by the metal radiating section 316a between the upper and lower members 317, 316 thus increasing the current density in the first and second layer 380a, 380b. The increasing magnetic field strength and increasing current densities eventually exceed the combined dielectric strength of the first and second layers 380a, 380b which results in the release of a burst of focused energy, that travels between the conductive tip 317a of the upper member 317 and the portion of the metal radiating section 316a of the lower member 316 closest to the conductive tip 317a.

The dielectric breakdown and the burst of focused energy through the first and second layers 380a, 380b of material effectively fuses a portion of the first layer 380a to a portion of the second layer 380b. Thus, the dielectric fusing apparatus 300 can effectively fuse together materials that do not normally bond.

The material fusing apparatus and method of use described herein and illustrated in FIG. 3 limits heating (and therefore fusing) to a very precise location, e.g., between the conductive tip 317a and the portion of the metal radiating section 316a adjacent the conductive tip 317a. This is often referred to as limiting thermal spread. As such, little heating takes place in the portion of the first and second layers 380a, 380b adjacent the fused portion so the dielectric fusing described hereinabove when used in the medical field provides reduced thermal spread. This method of energy transfer may be utilized in any medical procedure that requires a very precise amount of localized heat without impacting nearby tissue. For example, blood vessels and nerve strands may be fused closed with the apparatuses and methods disclosed herein with very minimal amounts of damage to the adjacent structures. Another application may be patching or fusing around blood vessels or any location requiring a fused patch, such as a leaking vertebral disk. The apparatuses and methods described herein may also be used in cosmetic surgery where tissue adhesion and blood vessel reconstruction aid greatly in the healing process but require delicate sutures or bonding methods. While fusing of patient tissue is one application of the material fusing apparatus of the present disclosure, other applications are contemplated by the present disclosure.

Figure 4A:
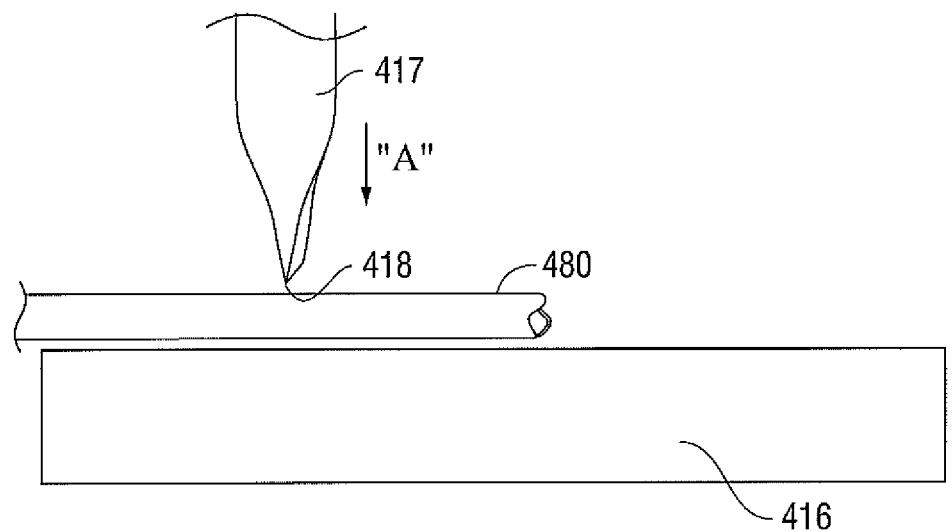
FIGS. 4A-4C are illustrations of a material fusing apparatus according to another embodiment of the present disclosure.
Figure 4B:
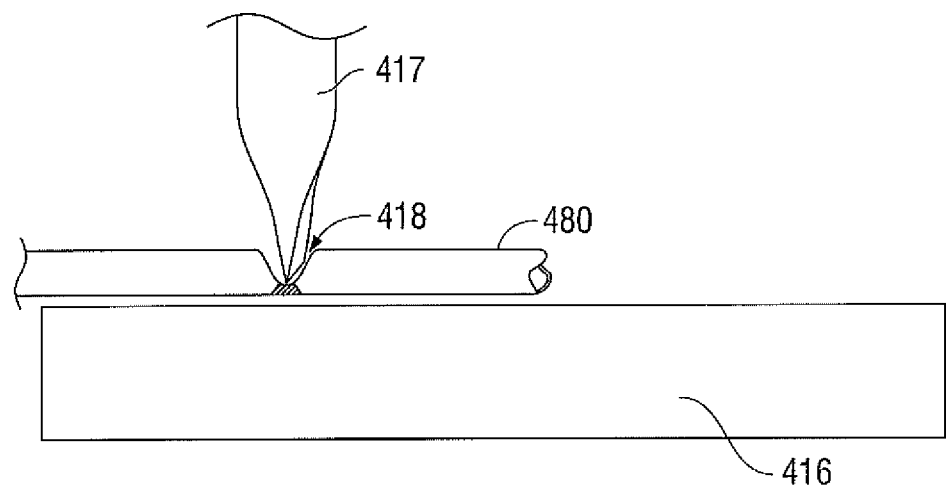
Figure 4C:
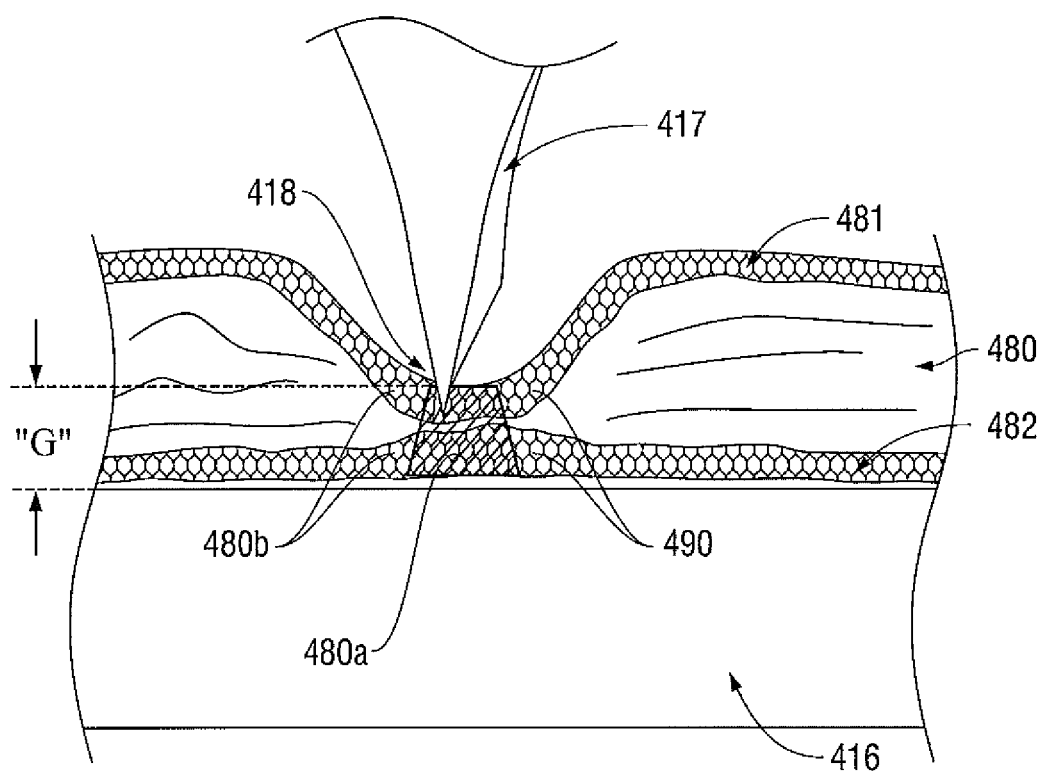

FIGS. 4A-4C further illustrate a tissue fusing method applied to a tubular body structure (e.g., a blood vessel or artery, a bronchial tube or lung tissue, a renal vessel or kidney tissue, a nerve strand of the peripheral nervous system or a tract of the central nervous system). In FIGS. 4A-4C the material fusing apparatus includes a metal radiating source 416 and a non-radiating fusing strike arm 417 that ends with a pointed conductive tip 418 at the distal end thereof. A tubular body structure 480 is placed between the metal radiating source 416 and the conductive tip 418.

In FIG. 4A the non-radiating fusing strike arm 417 moves toward the metal radiating source 416 as indicated by the single arrow "A" until the conductive tip 418 compresses the tubular structure against the metal radiating source 416, as illustrated in FIG. 4B. The amount of compression force, applied by the non-radiating fusing strike arm 417 to the tubular structure, must be sufficient to provide contact between the upper layer 481 and the lower layer 482 as illustrated in FIGS. 4B and 4C. When fusing is triggered, a portion of the upper layer 481 and a portion of the lower layer 482, between the conductive tip 418 and the metal radiating source 416, are fused together and form a fused area 480a, as illustrated in FIG. 4C. Fusing produces little heat energy in the adjacent healthy tissue 480b.

Fusing of the upper layer 481 and the lower layer 482 occurs when the energy level of the microwave energy signal is sufficient to dielectrically break down the material between the conductive tip 418 and the metal radiating source 416. The energy level required to fuse is dependant on the combined dielectric properties of the two layers 481, 482, the distance, or gap "G", between the conductive tip 418 and the metal radiating source 416 and the energy level of the microwave energy signal provided to the metal radiating source 416. For example, keeping the gap "G" constant, an increase in the dielectric strength of the materials will result in an increase in energy level required to fuse the two materials. Keeping the dielectric strength of the materials constant and decreasing the gap "G" will result in a decrease in the required energy level of the microwave signal. As such, the energy level required to fuse the material is related to at the gap "G" distance, the dielectric property of the material disposed between the metal radiating source 416 and the conductive tip 418 and/or the field concentration of the microwave energy.

In one embodiment, as the conductive tip 418 compresses the upper layer 481 and the lower layer 482, a portion of material is displaced from the gap "G". The portion of material displaced from the gap "G" may be fluid (e.g., air, blood, urine or other body fluid) or tissue. Displacing material thereby reduces the dielectric strength while the gap is being simultaneously reduced. As such, the energy level required to fuse the material and the dielectric properties of the material are directly proportional to the size of the gap "G" between the metal radiating source 416 and the conductive tip 418.

The fusing operation may be triggered manually by an operator such as, for example, a clinician. In one embodiment, the clinician positions the non-radiating fusing strike arm 417 in a suitable position and manually triggers fusing by initiating the delivery of a microwave energy signal, at a sufficient energy level, to the metal radiating source 416. In another embodiment, the microwave energy signal is initiated prior to the positioning of the non-radiating fusing strike arm 417 and the clinician applies a compression force to the strike arm until the position of the non-radiating fusing strike arm 417 is sufficiently close to the metal radiating source 416 to fuse the materials. The fusing operation may also be triggered automatically. A suitable force measuring device measures the pressure applied by the non-radiating fusing strike arm 417 as the strike arm 417 compresses the tubular body structure 480 against the metal radiating source 416. The delivery of a microwave energy signal may be automatically initiated after the applied pressure or the position of the radiating fusing strike arm 417 exceeds a threshold.

The energy level of the microwave energy signal may be related to the amount of force applied by the non-radiating fusing strike arm 417 on the tubular structure 480. For example, as the applied force of the non-radiating fusing strike arm 417 increases, the energy level of the microwave energy signal automatically increases, linearly or non-linearly, until the position of the non-radiating fusing strike arm 417 and the microwave signal energy level are sufficient to fuse the upper layer 481 and the lower layer 482.

Figure 5:
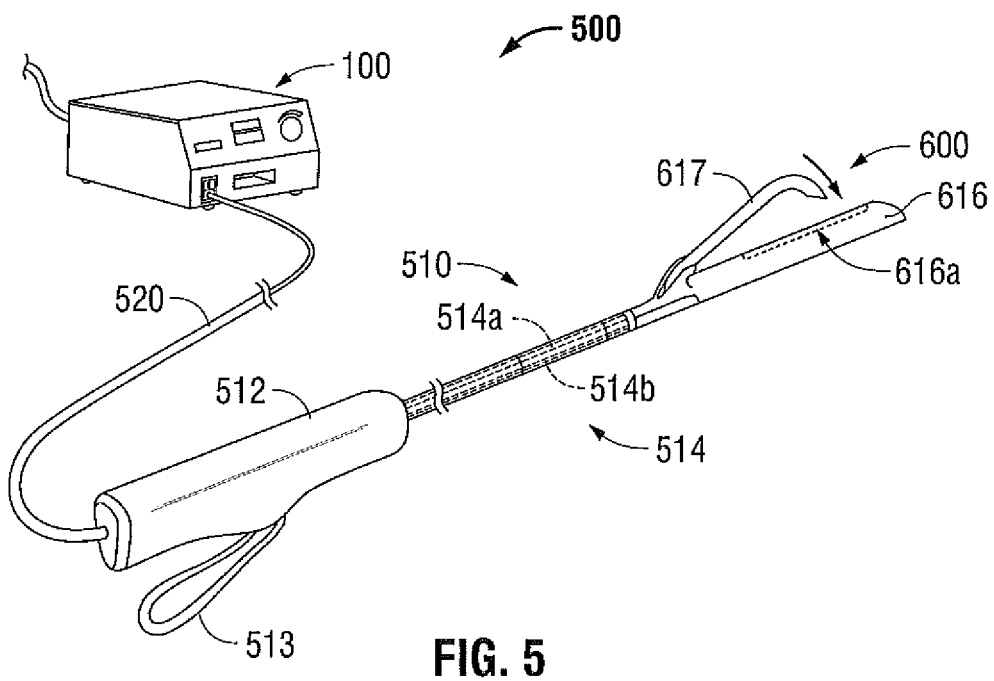
FIG. 5 is a schematically-illustrated view of a material fusing system including a microwave generator and a material fusing apparatus in accordance with one embodiment of the present disclosure.

Referring now to FIG. 5, a material fusing system is shown as system 500. System 500 includes a microwave signal generator 100 connected to a material fusing apparatus 510 via a transmission line 520.

Material fusing apparatus 510 includes a handle 512, a clamping trigger 513, an end effector 600 coupled to the handle by an elongated shaft 514. Handle 512 receives a microwave energy signal from the transmission line 520 connected to the proximal end. Elongated shaft is formed of a microwave waveguide 514a (e.g., a coaxial cable or other suitable waveguide) and an actuator shaft 514b. Microwave waveguide is configured to transmit a microwave signal from the handle 512 to the end effector 600 on the distal end of the elongated shaft 514. Actuator shaft 514b transfers mechanical movements of the clamping trigger 513 to the end effector 600 and is configured to manipulate the jaws of the end effector.

Figure 6A:
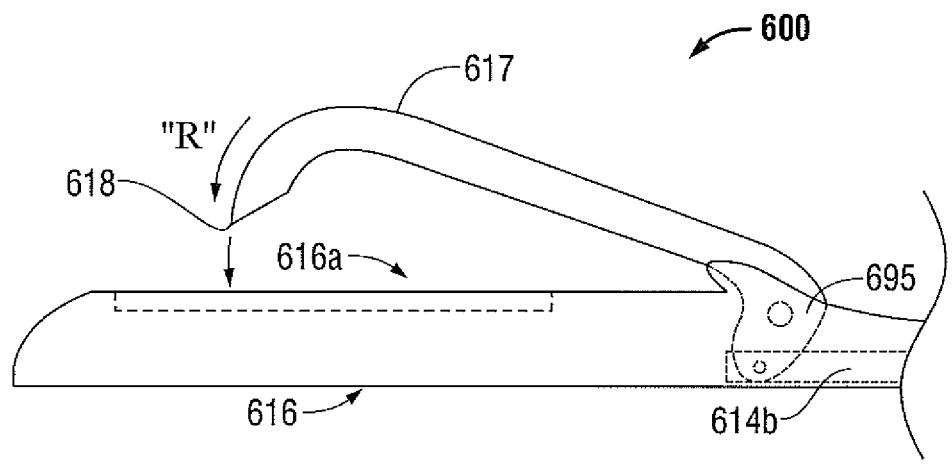
FIG. 6A is an illustrative, side view of an end effector of a material fusing apparatus according to one embodiment of the present disclosure.
Figure 6B:
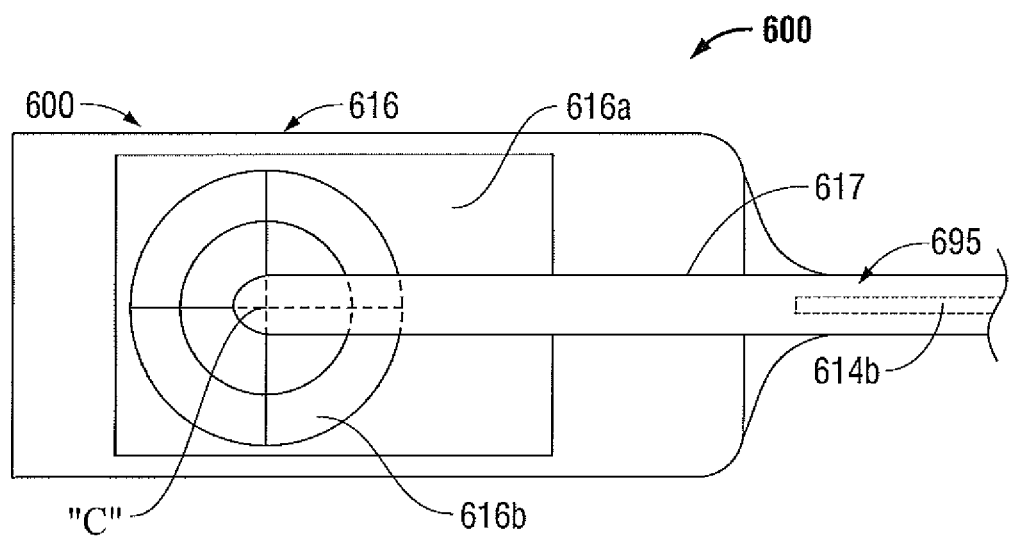
FIG. 6B is an illustrative, top view of the end effector of FIG. 6A.

FIG. 6A is an illustrative, side view of the end effector 600 of the material fusing apparatus 510 of FIG. 5 according to one embodiment of the present disclosure. FIG. 6B is an illustrative, top view of the end effector 600 of FIG. 6A. With reference to FIGS. 5, 6A and 6B, the end effector 600 includes two interfacing jaw members 617, 616 connected by a closure mechanism 695. End effector 600 includes a non-radiating fusing strike arm 617 with a conductive tip and a fixed radiating arm 616. The fixed radiating arm 616 includes a radiating metal strike plate 616a. The non-radiating fusing strike aim 617 includes a conductive tip 618. In one embodiment, hinge mechanism 695 pivotally connects non-radiating strike arm 617 to the fixed radiating arm 616 such that non-radiating strike arm 617 radially pivots around hinge mechanism 695 along an arc "R".

In a first condition, the closure mechanism 695 positions the fixed radiating arm 616 and the non-radiating strike plate 617 in a spaced-apart relationship (e.g., the two interfacing jaw members 616, 617 are open). In a second condition, the closure mechanism 695 positions the conductive tip 618 of the non-radiating fusing strike arm 617 adjacent a strike point on the radiating metal strike plate 616a, wherein the gap between the conductive tip 618 and the radiating metal strike plate 616a forms a material fusing gap therebetween.

Actuator shaft 514b connects the radiating fusing strike arm 617 to the clamping trigger 513 through the elongate shaft 514. Compression of the clamping trigger 513 toward the handle 512 draws the actuator shaft 514b toward the handle 512. Drawing the actuator shaft 514b toward the handle 512 rotates the radiating fusing strike aim 617 about the hinge mechanism 695 such that the conductive tip 618 moves toward the fixed radiating arm 616.

In use, the end effector 600 is positioned such that the target material (e.g., one or more tissue layers) is positioned on the radiating metal strike plate 616a. Radiating metal strike plate 616a may include positioning crosshairs 616b to aid in the positioning of the target material, wherein the center "C" of the positioning crosshairs 616b is the strike point (e.g., the position on the radiating metal strike plate 616a where the conductive tip 618 of the non-radiating fusing strike arm 618 and the radiating metal strike plate 616a form a material fusing gap).

With the target material properly positioned on the radiating metal strike plate 616a, the non-radiating fusing strike arm 617 is actuated toward the radiating metal strike plate 616a by the closing of the clamping trigger 513. The clamping trigger 513 slidably engages the actuator shaft 514b, 614b. Actuator shaft 514b, 614b pivotally engages the non-radiating fusing strike arm 617 and pivots the conductive tip 618 toward the center "C" of the positioning crosshairs 616b. The radiating metal strike plate 616a receives a microwave signal from the microwave generator 100 and the radiating metal strike plate 616a radiates microwave energy. As the conductive tip 618 approaches the radiating metal strike plate 616b, the strength of the magnetic field therebetween increases until one or more bursts of focused energy are transferred between the conductive tip 618 and the radiating metal strike plate 616b thereby fusing the target material therebetween.

Figure 7A:
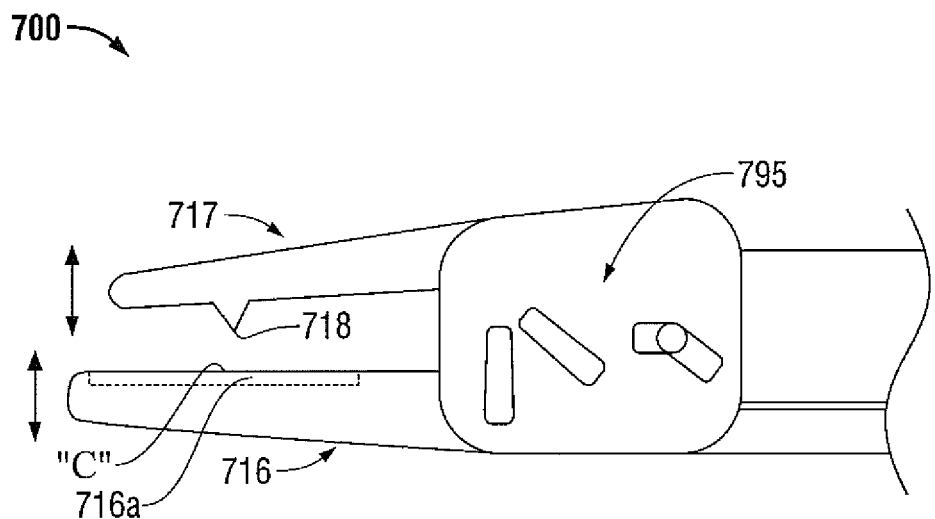
FIG. 7A is an illustrative, side view of the end effector of a material fusing apparatus having a parallel closure mechanism according to another embodiment of the present disclosure.
Figure 7B:
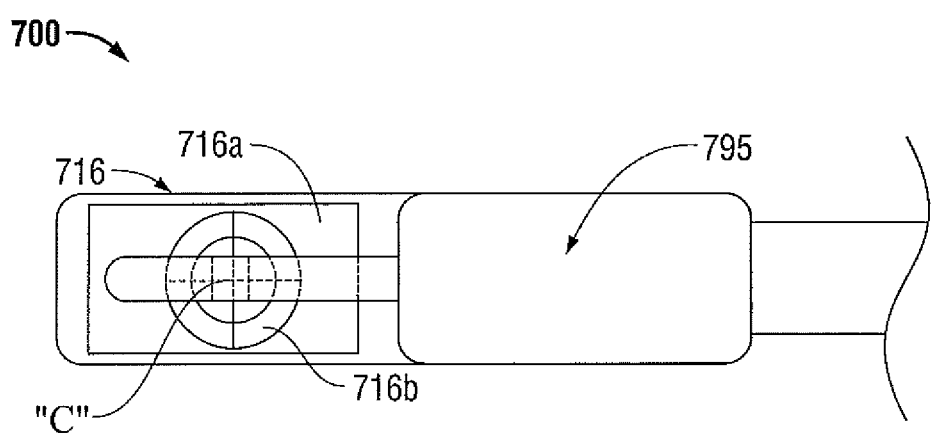
FIG. 7B is an illustrative, top view of the end effector of FIG. 7A.

FIG. 7A is an illustrative, side view of an end effector 700 of a material fusing apparatus according to another embodiment of the present disclosure. FIG. 7B is an illustrative top view of the end effector 700 of FIG. 7A. End effector 700 is configured to connect to the distal end of the material fusing apparatus 510 of FIG. 5. End effector 700 includes a non-radiating strike plate arm 717 and a radiating arm 716. Non-radiating strike plate arm 717 and radiating aim 716 are parallel to each other and are moved toward one another by a parallel closure mechanism 795. Non-radiating strike plate arm 717 includes a conductive tip 718 that aligns with the center "C" of the positioning crosshairs 716b of the metal radiating plate 716a of the radiating arm 716.

In use, target material is positioned between conductive tip 718 and center "C" of positioning crosshairs 716b. Non-radiating strike plate arm 717 and radiating aim 716 move toward one another by closing the clamping trigger 513 (See FIG. 5). As the conductive tip 718 of the non-radiating strike plate arm 717 approaches the center "C" of the positioning crosshairs 717b the radiating metal strike plate 716a receives a microwave signal from the microwave generator 100 and the radiating metal strike plate 716a radiates microwave energy. As the conductive tip 718 approaches the radiating metal strike plate 716b the strength of the magnetic field therebetween increases until one or more bursts of focused energy are transferred between the conductive tip 618 and the radiating metal strike plate 716b thereby fusing the target material therebetween.

In another embodiment, the end effector 700 may be attached to the distal end of a microwave energy delivery device. End effector 700 may capacitively coupled to the microwave antenna portion of a microwave energy delivery device and receive microwave energy therefrom.

The end effector 600, 700 with a single strike point (see FIGS. 6A-6B and 7A-7B, respectively) is only one means of creating a localized point seal using the fusing methods described in the present disclosure. Multiple edges and/or fusing points may be used to create a dielectric breakdown area of any desirable size and shape.

Figure 8A:
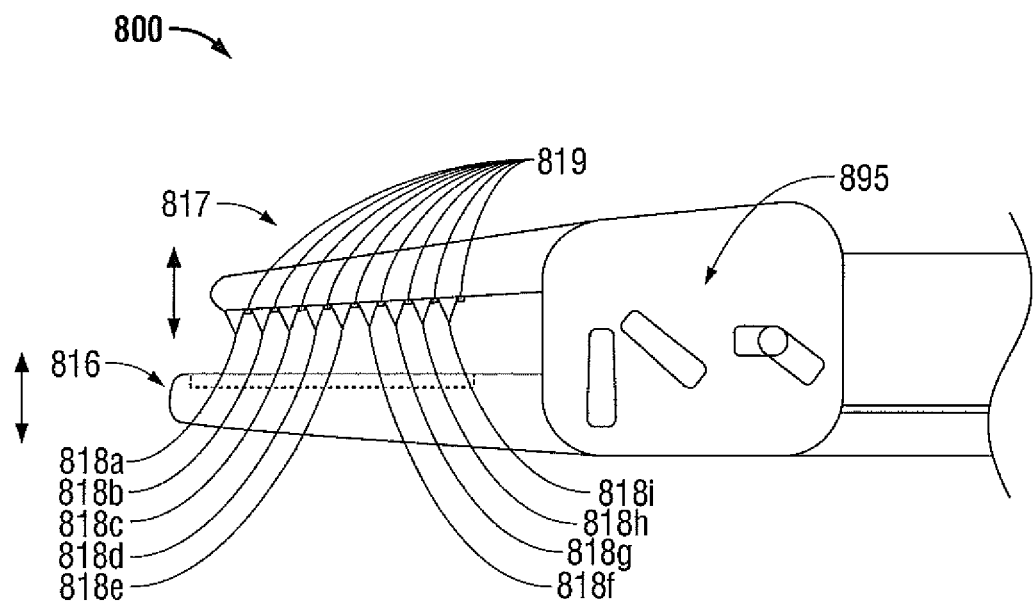
FIG. 8A is an illustrative, side view of an end effector of a material fusing apparatus, with a plurality of fusing points, according to another embodiment of the present disclosure.
Figure 8B:
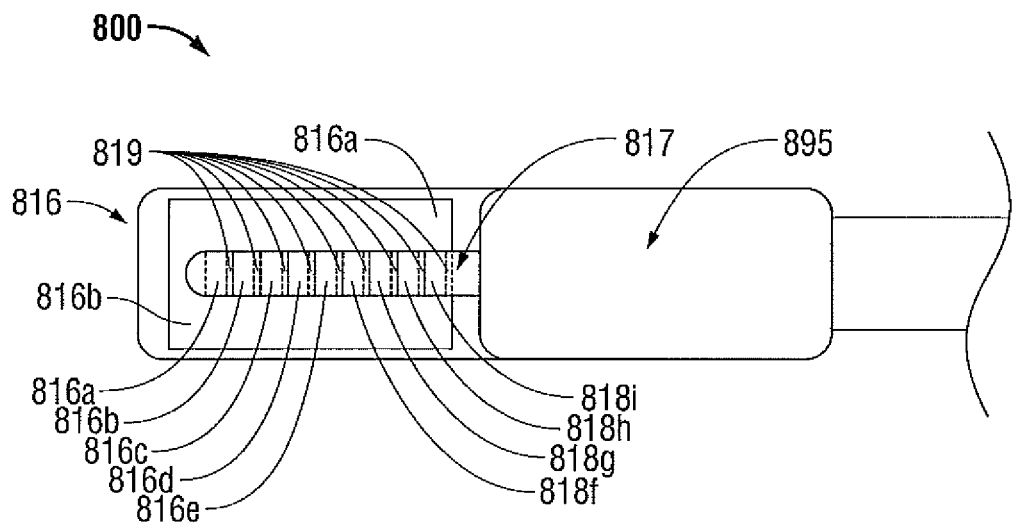
FIG. 8B is an illustrative top view of the end effector 800 of FIG. 8A.

FIG. 8A is an illustrative, side view of an end effector 800 of a material fusing apparatus, with a plurality of fusing points, according to another embodiment of the present disclosure, and FIG. 8B is an illustrative top view of the end effector 800 of FIG. 8A. End effector 800 may be configured to connect to the distal end of the material fusing apparatus 510 of FIG. 5. End effector 800 includes a non-radiating strike plate arm 817 and a radiating arm 816. Non-radiating strike plate arm 817 includes a plurality of conductive tips 818a-818i each configured to conduct microwave energy as discussed hereinabove. Conductive tips 818a-818i may be separated by a non-conducting spacer 819 such that each of the conductive tips 818a-818i is independent and insulated from an adjacent conductive tip (or tips).

In use, end effector 800 is configured to generate a series of fusing points as described hereinabove. The configuration of the conductive tips 818a-818i (e.g., the size, shape and spacing therebetween) may be adjusted to achieve a desired effect. For example, the points may be configured to make a elongated seal, a resection line, a curved fusion line or any other desirable configuration.

In one embodiment, the individual conductive tips 818a-818i are configured to simultaneously fuse material. In another embodiment, fusing is performed sequentially. Sequential fusing may be triggered by grounding one or more of the conductive tip 818a-818i or by independently actuating one or more conductive tips 818a-818i toward the radiating arm 816.

As various changes could be made in the above constructions without departing from the scope of the disclosure, it is intended that all matter contained in the above description shall be interpreted as illustrative and not in a limiting sense. It will be seen that several objects of the disclosure are achieved and other advantageous results attained, as defined by the scope of the following claims.

What is claimed is:

1. A microwave material fusing apparatus, comprising:
   an end effector including:
      a strike plate that receives a microwave energy signal from a microwave energy source and radiates microwave energy therefrom upon selective activation of the microwave energy source; and
      a fusing arm disposed in substantial opposition to the strike plate, the fusing arm including a pointed conductive tip formed with a conductive material on a distal end thereof,
   wherein the pointed conductive tip of the fusing arm and the strike plate are selectably movable relative to one another between an open position and a closed position in which the pointed conductive tip of the fusing arm is oriented perpendicularly relative to the strike plate and only the pointed conductive tip of the fusing arm and the strike plate compress a material disposed therebetween such that upon activation of the microwave energy source, microwave energy is transferred between the strike plate and the pointed conductive tip to fuse the material disposed therebetween.

2. A microwave material fusing apparatus according to claim 1, wherein the end effector is configured to release a burst of focused energy that travels between the pointed conductive tip and the strike plate to fuse the material.

3. A microwave material fusing apparatus according to claim 2, wherein the end effector further includes:
   a closure mechanism connected to the strike plate and the fusing arm,
   wherein in the open position, the closure mechanism positions the strike plate and the fusing arm in a spaced-apart relationship, and
   wherein in the closed position, the closure mechanism positions the strike plate and the pointed conductive tip such that a material fusing gap is formed therebetween.

4. A microwave material fusing apparatus according to claim 3, wherein the material fusing gap between the strike plate and the pointed conductive tip of the fusing arm in the closed position is related to at least one of a property of the material therebetween, the density of the radiated microwave energy and the amount of energy delivered to the material.

5. A microwave material fusing apparatus according to claim 3, wherein the energy level of the microwave energy signal is related to the material fusing gap between the pointed conductive tip and the strike plate and a dielectric property of the material between the pointed conductive tip and the strike plate.

6. A microwave material fusing apparatus according to claim 3, wherein the microwave energy is transferred between only the pointed conductive tip and a strike point of the strike plate.

7. A microwave material fusing apparatus according to claim 6, wherein the strike point is a radial center formed on the strike plate.

8. A microwave material fusing apparatus according to claim 3, wherein material fusing is initiated after the material fusing gap meets a threshold distance between the pointed conductive tip and the strike plate.

9. A microwave material fusing apparatus according to claim 3, wherein the closure mechanism is pivotally attached to the strike plate and to the fusing arm, wherein the strike plate and the fusing arm rotate relative to one another to compress the material.

10. A microwave material fusing apparatus according to claim 3, wherein the closure mechanism is slidably attached to the radiating strike plate and the non-radiating fusing arm such that the radiating strike plate and the non-radiating fusing arm rotate relative to one another in a parallel manner to compress the material.

11. A microwave material fusing apparatus according to claim 3, wherein the end effector further includes:
   a clamping trigger connected to the closure mechanism and configured to actuate the closure mechanism between the open position and the closed position.

12. A microwave material fusing apparatus according to claim 1, wherein material fusing is initiated after an applied pressure applied to the material exceeds a threshold.

13. A method of fusing material, comprising the steps of:
   providing an end effector including a strike plate that receives a microwave energy signal from a microwave energy source and radiates microwave energy therefrom upon selective activation of the microwave energy source and a fusing arm disposed in substantial opposition to the strike plate, the fusing arm including a pointed conductive tip formed with a conductive material on a distal end thereof wherein the pointed conductive tip of the fusing arm and the strike plate are selectably movable relative to one another between an open position and a closed position in which the pointed conductive tip of the fusing arm is oriented perpendicularly relative to the strike plate and only the pointed conductive tip of the fusing arm and the strike plate compress a material disposed therebetween;
   compressing the material between only the strike plate and the pointed conductive tip of the fusing arm; and
   activating the microwave energy source to transmit energy between the strike plate and the pointed conductive tip to fuse the material disposed therebetween.

14. A microwave material fusing apparatus according to claim 1, wherein in the closed position, only an endmost edge of the pointed conductive tip of the fusing arm and the strike plate compress the material therebetween.

15. A method of fusing material according to claim 13, wherein in the closed position, only an endmost edge of the pointed conductive tip of the fusing arm and the strike plate compress the material therebetween.

* * * * *